(12) United States Patent
Marold

(10) Patent No.: US 9,060,833 B2
(45) Date of Patent: Jun. 23, 2015

(54) METHOD OF PREPARING FLAVORED FUNCTION SPECIFIC TOOTHPICK

(71) Applicant: H2X, Inc., Tucson, AZ (US)

(72) Inventor: Vincent J. Marold, Tucson, AZ (US)

(73) Assignee: H2X, INC., Tuscon, AZ (US)

( * ) Notice: Subject to any disclaimer, the term of this patent is extended or adjusted under 35 U.S.C. 154(b) by 0 days.

(21) Appl. No.: 14/139,224

(22) Filed: Dec. 23, 2013

(65) Prior Publication Data
US 2014/0109929 A1  Apr. 24, 2014

Related U.S. Application Data

(63) Continuation of application No. 13/789,198, filed on Mar. 7, 2013, now abandoned.

(30) Foreign Application Priority Data

Mar. 7, 2012 (WO) ................ PCT/US2012/028140

(51) Int. Cl.
*A61C 15/00* (2006.01)
*A45D 7/00* (2006.01)
*A61C 15/02* (2006.01)

(52) U.S. Cl.
CPC ....................................... *A61C 15/02* (2013.01)

(58) Field of Classification Search
CPC ...... A61C 15/02; A61C 15/00; A61C 15/041; A61C 15/046; A61C 17/00
USPC ......... 132/321, 329, 333, 200, 309, 318, 320; 427/254, 314, 325, 2.29, 317, 440, 427/444; 433/141, 215, 216; 428/541; 424/49; 144/380
See application file for complete search history.

(56) References Cited

U.S. PATENT DOCUMENTS

| | | | | | |
|---|---|---|---|---|---|
| 174,619 | A | * | 3/1876 | Clark | 132/321 |
| 410,794 | A | * | 9/1889 | Hellwig | 132/321 |
| 656,479 | A | * | 8/1900 | Schellenbach | 132/321 |
| 1,768,175 | A | * | 6/1930 | Vivas | 427/297 |
| 2,414,808 | A | * | 1/1947 | Hamill | 144/380 |
| 2,668,779 | A | * | 2/1954 | Herman | 427/297 |
| 3,284,157 | A | * | 11/1966 | Peters | 427/317 |
| 3,720,762 | A | | 3/1973 | Hatasa et al. | |
| 3,968,276 | A | * | 7/1976 | Allen | 427/297 |
| 4,108,226 | A | * | 8/1978 | Bornstein | 144/380 |
| 4,276,329 | A | * | 6/1981 | Vasishth et al. | 427/393 |
| 4,846,200 | A | * | 7/1989 | Wiley | 132/321 |
| 4,942,034 | A | * | 7/1990 | Hill et al. | 424/401 |
| 5,002,077 | A | * | 3/1991 | Wiley | 132/321 |
| 5,875,798 | A | * | 3/1999 | Petrus | 132/321 |
| 5,882,427 | A | * | 3/1999 | Michanickl et al. | 134/6 |
| 2005/0058609 | A1 | * | 3/2005 | Nazeri | 424/49 |
| 2005/0287231 | A1 | * | 12/2005 | Nussen | 424/729 |
| 2006/0048852 | A1 | | 3/2006 | McIntosh | |
| 2006/0162732 | A1 | * | 7/2006 | Winn et al. | 131/271 |
| 2006/0249174 | A1 | * | 11/2006 | Finger et al. | 132/321 |
| 2007/0000514 | A1 | * | 1/2007 | O'Shaughnessey et al. | 132/321 |
| 2007/0181144 | A1 | * | 8/2007 | Brown et al. | 132/321 |
| 2010/0143739 | A1 | * | 6/2010 | Willems | 428/541 |

FOREIGN PATENT DOCUMENTS

EP   351145 A2 * 1/1990 ............. A61C 15/02

OTHER PUBLICATIONS

Search Report dated Apr. 28, 2014.

* cited by examiner

*Primary Examiner* — Vanitha Elgart
(74) *Attorney, Agent, or Firm* — Abelman, Frayne & Schwab

(57) ABSTRACT

A flavored toothpick and a method for preparing such, the product exhibiting improved capacity for delivering flavor and additives to the user, among other advantages. The toothpick may be prepared by pretreating the wooden substrate to increase porosity and decrease hardness. The toothpick is then immersed in a solution containing an additive, a masking agent, and a sweeting agent, where the toothpick absorbs the solution. Alternatively, the toothpick may be placed with the solution in a sealed chamber under vacuum pressure to infuse the toothpick with the additive solution and any desired flavoring.

18 Claims, 3 Drawing Sheets

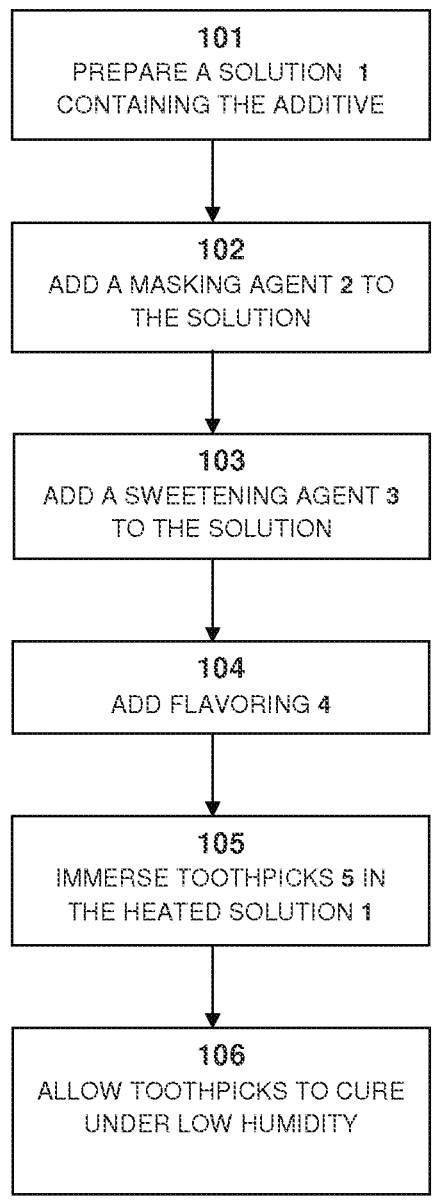

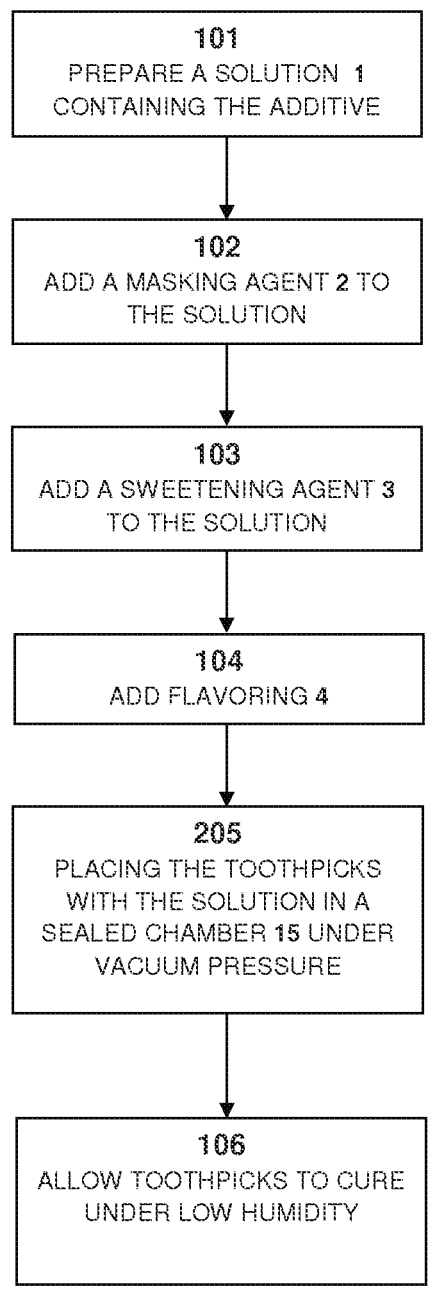

US 9,060,833 B2

METHOD OF PREPARING FLAVORED FUNCTION SPECIFIC TOOTHPICK

CLAIM OF PRIORITY

This application is a continuation of and claims benefit to U.S. application Ser. No. 13/789,198, filed on Mar. 7, 2013, entitled "Flavored Function Specific Toothpicks", which claims the benefit of PCT patent application PCT/US2012/028140, filed Mar. 7, 2012, the entirety of which are hereby incorporated by reference.

FIELD OF THE INVENTION

The present disclosure relates generally to dental implements and, more particularly, to flavored toothpicks and a method for making the same.

BACKGROUND OF THE INVENTION

Toothpicks have been used as a dental implement by man for centuries. Numerous studies in recent history have demonstrated that toothpicks are comparable to other dental implements at cleaning teeth effectively. In fact, toothpicks are much easier to use than dental floss and are thus much more likely to be used by children and the elderly to promote dental health. Further, many suggest that the use of toothpicks may facilitate the overcoming of oral fixations such as smoking, over-eating, and the like.

Toothpicks are typically formed as slivers of material, such as birch wood, having at least one end that is pointed for inserting in between the user's teeth. There are several methods currently available by which a toothpick can be manufactured to include other features, such as a flavor or helpful additive, such as fluoride. These methods typically involve coating or dusting the toothpick with a flavored compound or oil. However, these products generally lose their flavor and the effectiveness of any other additives in a relatively short time frame.

Accordingly, there remains a need to produce a toothpick with a greater ability to hold and to effectively deliver flavoring agents and other additives.

SUMMARY OF THE INVENTION

The present disclosure provides a flavored toothpick and a method for preparing such, the product fulfilling the need for a greater capacity and effectiveness in delivering flavoring and other desired additives. Other advantages in performance will be apparent to one having ordinary skill in the art.

In a first aspect, the present disclosure provides a flavored toothpick, formed as a single piece of substrate from a wood material. The wooden substrate is pretreated to achieve an increase in porosity and a decrease in hardness. The pretreatment is performed with a wash of warm water, which may also include other chemicals to aid in the process, such as sodium hydroxide (NaOH). The hardness of the toothpick is typically decreased by more than 50% while the porosity is increased by more than 30%.

A second aspect of the present disclosure provides a method of preparing a flavored toothpick, where the toothpick is placed in a pretreatment wash as described above, and wherein the toothpick is placed in an additive solution at a raised temperature before curing the toothpick in an environment of low humidity.

Yet another aspect of the disclosure provides a method for preparing a flavored toothpick wherein flavoring and/or additives are infused into the substrate by placing the toothpick in a sealed chamber with the flavoring/additive solution under a vacuum. The toothpicks are then cured in a low humidity environment with heated forced air.

BRIEF DESCRIPTION OF THE DRAWINGS

Further features and advantages of the present disclosure will be seen from the following detailed description, taken in conjunction with the accompanying drawings, wherein:

FIG. 2 is a flowchart displaying a method of preparing a flavored toothpick in accordance with another aspect of the present disclosure; and FIG. 3 is a flowchart displaying a method of preparing a flavored toothpick using vacuum pressure in accordance with another aspect of the present disclosure.

DETAILED DESCRIPTION OF THE INVENTION

Figure 1:
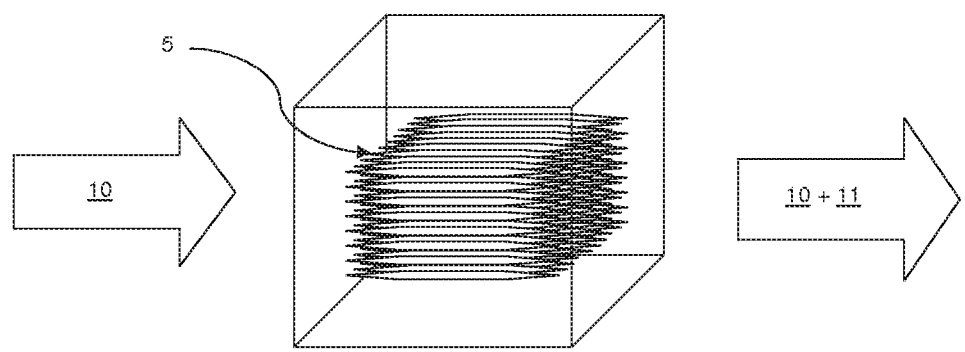
FIG. 1 is a schematic displaying a method for treating a toothpick substrate according to a first aspect of the present disclosure.

In the following description, reference is made to the accompanying drawings, which form a part hereof, and in which is shown, by way of illustration, various embodiments of the present disclosure. It is understood that other embodiments may be utilized and changes may be made without departing from the scope of the present invention.

In a first aspect, the present disclosure provides an improved flavored toothpick. The toothpick is may be made from any number of substrates, but the present discussion will reference birch wood, which is the most common toothpick material used in North America. Compared to conventional toothpicks, the flavored function specific toothpicks of the present disclosure are softer and able to absorb a larger amount of flavoring and other desired additives. These improved characteristics are the direct result of a pretreatment of the birch wood prior to the flavoring step. This pretreatment of the wood removes certain constituents of the wood structure to bring about the softer feel and increased porosity. The increased porosity allows the toothpick to absorb an increased amount of flavoring or other additives. The increased softness is appealing to many toothpick users because it reduces the risk of injuring the user's gums.

Referring to FIG. 1, the wood is pretreated by placing a batch of previously manufactured toothpicks 5 in a wash 10 of warm water. The water should be flowing, or at least agitated, in order to carry away "heavy cellulose" and other constituents 11 of the wood. For example, a batch of birch wood toothpicks is placed in a wash of water at a temperature of approximately 150° F. for approximately 1-2 hours. This process typically reduces the hardness of the final toothpick by over 50% compared to conventional toothpicks. While typical birch wood has a hardness of approximately 1260 lbs (as measured using the "Janka" test), the flavored toothpicks in accordance with the present disclosure exhibit hardness levels of approximately 300-500 lbs. Further, the same birch wood is estimated to have an increased porosity of over 30%, as observed by the additional uptake of injected material. Other organic materials may be similarly treated, exhibiting increased porosity of 10% or greater.

In order to decrease the wash time or temperature, or to target specific constituents of a particular toothpick substrate, the wash may also include other chemically active substances. For example, the pH of the wash may be slightly basic by adding a dilute solution of sodium hydroxide (NaOH) or sodium bicarbonate to result in a solution with pH above 7. This will target the cellulose structure of wood. In general, a basic solution is preferable because of its potential to remove portions of the cellulose, thereby increasing the porosity, without otherwise compromising the structural integrity of the wood. However, acidic solutions may also be used with wood to remove other constituents. Other chemical specific solutions may also be used with wood or other substrates as necessary or desired.

In another aspect, the present disclosure provides a process for making the flavored toothpicks described above. With reference to FIG. 2, a toothpick in accordance with the disclosure is made by first preparing a super-saturated solution 1 of the desired additive (step 101). For example, a super-saturated caffeine solution is prepared by heating water to an elevated temperature sufficient to dissolve caffeine, for example between 140 and 180 degrees Fahrenheit. Once the desired additive has been dissolved, a masking agent 2 is added to the solution to mask any undesired flavor characteristics of the additive (step 102). Next, a sweetening agent 3 is added (step 103). Finally, 104 the flavoring 4 is added.

The desired additive may be caffeine, as mentioned above, or may be one or more of a number of biologically active compounds suitable for ingestion and having a variety of advantageous features. For example, in addition to caffeine, such biologically active compounds include a variety of botanicals, vitamins, homeopathic compounds, synthetic compounds, and the like, such as are now known—or come to be known—as suitable additives or nutritional supplements. Such compounds may also include addictive compounds such as nicotine or other chemicals, wherein the dental implement disclosed herein may be useful as an addiction recovery aid.

The solution may be water-based or alcohol-based, depending on the characteristics of the additive and flavoring considerations. The length of time that the solution remains at the elevated temperature is also dependent upon the characteristics of the additive and other constituents. Next, the toothpicks 5 are added to the heated solution and allowed to soak therein for a period of time sufficient for the solution to be fully absorbed into the toothpick (step 105).

In the example of the caffeinated toothpicks, the toothpicks are added to the heated solution and allowed to soak therein for a period of time sufficient for the solution to substantially permeate the matrix of the toothpick substrate. For example, the toothpicks may be added to the heated solution and left to soak therein for a period of time, such as, for example, a period of approximately three hours. During this time, the temperature of the solution is preferably maintained at approximately 140 degrees Fahrenheit or greater.

The infused toothpicks are then removed from the solution, drained and allowed to dry under conditions of low relative humidity 106. The low humidity environment should be less than 18% relative humidity, but is preferably about 8-12% relative humidity. To expedite the drying process forced air, heated air, or a combination thereof may be used to increase the rate at which the picks give up the moisture contained therein. By way of example, forced air may be alternately forced into or drawn from the chamber. Using this method, the toothpicks of the present disclosure should be sufficiently cured within about one hour.

In the caffeine example, the solution will be comprised of approximately 50-70% water, 15-25% flavoring agent, 1-3% masking agent, 1-3% artificial sweetener (powder), and 7-10% caffeine (anhydrous). These amounts are approximate and will vary depending on the additive, the form it is provided in, and the base of the solution (water, alcohol, or otherwise). For instance, the artificial sweetener need not be provided in powder form, but could instead be provided as a liquid, and thereby comprise a greater volume percentage of the overall solution.

The flavoring agent may be a natural or artificial flavor. For example, the flavoring agent may be a water-soluble flavoring agent and may be comprised of one or more constituents, including, for example: almond flavor, almond toffee flavor, amaretto flavor, apple flavor, apple pie flavor, apricot crème flavor, bailey's Irish cream flavor, baklava flavor, banana flavor, banana cream flavor, banana nut bread flavor, bananas foster flavor, almond biscotti flavor, chocolate biscotti flavor, lemon & icing biscotti flavor, vanilla nut biscotti flavor, brown sugar flavor, black cherry flavor, triple berry flavor, bourbon flavor, Butterfinger™ flavor, butter cream flavor, butter pecan flavor, butter fum flavor, butterscotch flavor, caramel flavor, caramel apple flavor, caramel latte flavor, caramel macchiato flavor, chai flavor, cherry flavor, chocolate flavor, chocolate cream flavor, chocolate mint flavor, chocolate raspberry flavor, cinnamon flavor, coconut flavor, coconut crème flavor, coconut & rum flavor, cranberry flavor, crème brulee flavor, crème dementhe flavor, dulce de leche flavor, egg nog flavor, English toffee flavor, espresso flavor, frangelica flavor, french vanilla flavor, green tea flavor, hazelnut flavor, grand marnier flavor, highland grogg flavor, honey flavor, Irish cream flavor, Kona flavor, lemon drops flavor, licorice flavor, lime flavor, macadamia nut flavor, mandarin orange flavor, mango flavor, margarita flavor, marshmallow flavor, mocha flavor, passion fruit flavor, peach flavor, peaches and cream flavor, pear flavor, peppermint flavor, pineapple flavor, pina colada flavor, pistachio flavor, pomegranate flavor, praline flavor, pumpkin pie flavor, rain forest crunch flavor, raspberry flavor, rose flavor, rum flavor, Santa's Xmas flavor, Snickers™ flavor, snickerdoodle flavor, swiss chocolate almond flavor, spice flavor, strawberry flavor, oil-based sweetener flavor, sweet potato pie flavor, Tahitian vanilla flavor, tangerine flavor, tiramisu flavor, toasted almond flavor, toasted coconut flavor, vanilla flavor, vanilla spiced rum flavor, viennese flavor and white chocolate flavor.

The sweetening agent may be any suitable natural or artificial sweetener. In some examples, the sweetening agent is an artificial sweetener, selected from the group consisting of sucralose, aspartame, saccharin and acesulfame potassium.

The masking agent may be any suitable masking agent known in the art which is used in pharmaceutical supplements, foods and drinks to mask bitterness and/or enhance flavors. In one example, the masking agent is thaumatin or a derivative thereof. Thaumatin is a low calorie flavor modifier comprised of a natural protein extracted from the katemfe fruit, *Thaumatococcus daniellii*.

In one example of this aspect of the disclosure, the toothpicks are pretreated to increase the porosity and softness of the substrate. As discussed above, the substrate is pretreated, prior to the addition of the additive solution, by placing a batch of previously manufactured toothpicks 5 in a wash 10 of warm water. In order to decrease the wash time or temperature, or to target specific constituents of a particular toothpick substrate, the wash may also include other chemically active substances, including acids, bases, and the like.

Referring to FIG. 3, another example of the present aspect of the disclosure uses vacuum pressure to infuse the flavoring and additives into the porous substrate of the toothpick (step 205). For purposes of the present disclosure, the word "infuse" refers specifically to the use of vacuum pressure to force the flavoring and/or the additive solution to fill the porous structure of the substrate. Using this process, it is possible to achieve a nearly homogeneous distribution of additives and/or flavoring throughout the substrate.

By way of example, a batch of toothpicks is placed in a bath of the additive solution in a sealed chamber 15. A vacuum is applied to the chamber, for example, using a mechanical pump or compressor. Other machinery, such as liquid ring vacuum pumps may also be used, with varying amounts of pressure depending on the size of the batch, the strength of the material, and the solution.

While a small amount of pressure may be effective to significantly increase the uptake of the additive/flavoring, application of a vacuum of more than 10% below atmospheric pressure is useful to ensure that the substrate is fully saturated with the solution prior to the curing step 106.

Alternatively, the vacuum step 205 may be used in connection with the pretreatment of the toothpick substrate. The resulting toothpicks absorb approximately 50-85% more of the additive and/or flavoring solutions, whether water or alcohol-based. Toothpicks prepared according to this process may also exhibit other features, including decreased hardness and increased size (girth). The toothpicks therefore deliver significantly more of the desired additive and the increased flavoring is long-lasting, having been infused into the substrate.

It should be emphasized that the above-described embodiments of the present device and process, particularly, and "preferred" embodiments, are merely possible examples of implementations and merely set forth a clearer understanding of the principles of the disclosure. Many different aspects of the disclosure described herein may be designed and/or fabricated without departing from the spirit and scope of the disclosure. For example, the above disclosure discusses birch wood as the substrate from which the toothpick is formed, but several other materials, both organic and man-made are well within the scope of the present disclosure, in accordance with the skill in the art. All these and other such modifications and variations are intended to be included herein within the scope of this disclosure and protected by the following claims. Therefore the scope of the disclosure is not intended to be limited except as indicated in the appended claims.

The invention claimed is:

1. A method of preparing a flavored toothpick, the toothpick being formed of a substrate of unitary construction, the method comprising the steps of:
    pretreating the toothpick in a wash comprising a solution with pH above 7 to increase the porosity of the substrate;
    preparing an additive solution;
    placing the toothpick in the additive solution at a temperature of approximately 150° F. for a predetermined length of time; and
    curing the toothpick in a low humidity environment.

2. The method of claim 1, wherein the wash is flowing or agitated so that heavy cellulose and other constituents of wood of the toothpick are carried away.

3. The method of claim 1, wherein the additive solution is water-based.

4. The method of claim 1, wherein the step of pretreating the toothpick also results in a decrease in the hardness of the substrate.

5. The method of claim 1 wherein the additive solution is a biologically active compound.

6. The method of claim 1, wherein the additive solution contains a masking agent.

7. The method of claim 1, wherein the additive solution contains a sweetening agent.

8. The method of claim 1, wherein the additive solution comprises a flavoring.

9. The method of claim 1, wherein the step of curing the toothpick is performed in an environment of less than 18% relative humidity.

10. A method of preparing a flavored toothpick, the toothpick being formed of a substrate of unitary construction, the method comprising the steps of:
    pretreating the toothpick in a flowing or agitated wash, so that heavy cellulose and other constituents of wood of the toothpick are carried away, to increase the porosity of the substrate;
    preparing an additive solution;
    placing the toothpick in the additive solution at a temperature of approximately 150° F. for a predetermined length of time; and
    curing the toothpick in a low humidity environment.

11. The method of claim 10, wherein the wash comprises a solution with pH above 7.

12. The method of claim 10, wherein the additive solution is water-based.

13. The method of claim 10, wherein the step of pretreating the toothpick also results in a decrease in the hardness of the substrate.

14. The method of claim 10 wherein the additive solution is a biologically active compound.

15. The method of claim 10, wherein the additive solution contains a masking agent.

16. The method of claim 10, wherein the additive solution contains a sweetening agent.

17. The method of claim 10, wherein the additive solution comprises a flavoring.

18. The method of claim 10, wherein the step of curing the toothpick is performed in an environment of less than 18% relative humidity.

* * * * *